United States Patent
Damarati

(10) Patent No.: US 6,858,014 B2
(45) Date of Patent: Feb. 22, 2005

(54) MULTIPLE BIOPSY DEVICE

(75) Inventor: John Jairo Damarati, Tokyo (JP)

(73) Assignee: SciMed Life Systems, Inc., Maple Grove, MN (US)

( * ) Notice: Subject to any disclaimer, the term of this patent is extended or adjusted under 35 U.S.C. 154(b) by 234 days.

(21) Appl. No.: 10/118,202

(22) Filed: Apr. 5, 2002

(65) Prior Publication Data

US 2003/0191413 A1 Oct. 9, 2003

(51) Int. Cl.[7] .............................................. A61B 10/00
(52) U.S. Cl. ........................ 600/565; 600/564; 600/127; 600/129
(58) Field of Search .................................. 600/104, 562, 600/564, 565, 566, 567, 568, 105, 106, 107, 121, 123, 127, 129; 604/22; 606/167, 170, 171

(56) References Cited

U.S. PATENT DOCUMENTS 5,106,364 A * 4/1992 Hayafuji et al. ............ 606/171
5,409,012 A * 4/1995 Sahatjian ................... 600/562
6,142,956 A   11/2000 Kortenbach et al.

FOREIGN PATENT DOCUMENTS

WO    WO 97/24070 A1    7/1997
WO    WO 00/44285 A1    8/2000

* cited by examiner

*Primary Examiner*—Max F. Hindenburg
*Assistant Examiner*—Jonathan Foreman
(74) *Attorney, Agent, or Firm*—Christensen O'Connor Johnson Kindness PLLC

(57) ABSTRACT

A multiple biopsy device has a number of chambers into which tissue samples are received. A cutting mechanism, such as a blade, moves relative to the chambers to cut a tissue sample that is within a chamber. In one embodiment of the invention, the multiple biopsy device is removably secured to the distal end of an endoscope/bronchoscope.

12 Claims, 2 Drawing Sheets

MULTIPLE BIOPSY DEVICE

FIELD OF THE INVENTION

The present invention relates to medical devices and in particular to devices for obtaining biopsy samples from interior body cavities.

BACKGROUND OF THE INVENTION

In addition to obtaining a visual inspection with an endoscope/bronchoscope, etc., many physicians will biopsy a region of interest in order to confirm or deny the presence of disease.

The conventional method of obtaining a tissue sample is with a biopsy forceps. Most forceps have an elongated shaft that terminates at a sharp cutter with a tissue receptacle at the distal end. The forceps are threaded through a biopsy channel of the endoscope and a tissue sample is obtained. The forceps are then withdrawn from the endoscope and an assistant picks out the sample with a tweezers and places it in a numbered collection device so that the location of the tissue sample can be traced. The forceps are then reinserted in the endoscope to collect another sample at another collection point. This process is not only time consuming but adds wear and tear on the endoscope caused by the repeated insertion and withdrawal of the forceps.

There exist some biopsy forceps that hold multiple tissue samples in a single receptacle. However, they are not commonly used because the samples may commingle resulting in a loss of traceability. In addition, there is some chance that the samples may cross contaminate each other.

Given these problems there is a need for a multiple biopsy device that can easily obtain multiple tissue samples without requiring the device to be repeatedly withdrawn and inserted into the patient and will not commingle or cross contaminate the tissue samples.

SUMMARY OF THE INVENTION

A device for obtaining multiple biopsy samples from a patient has a cap positioned at the distal end of an endoscope. The cap has two or more chambers in which tissue samples are received. A cutter cuts tissue that has entered a chamber. The chamber is then sealed and another chamber is positioned to receive another tissue sample.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
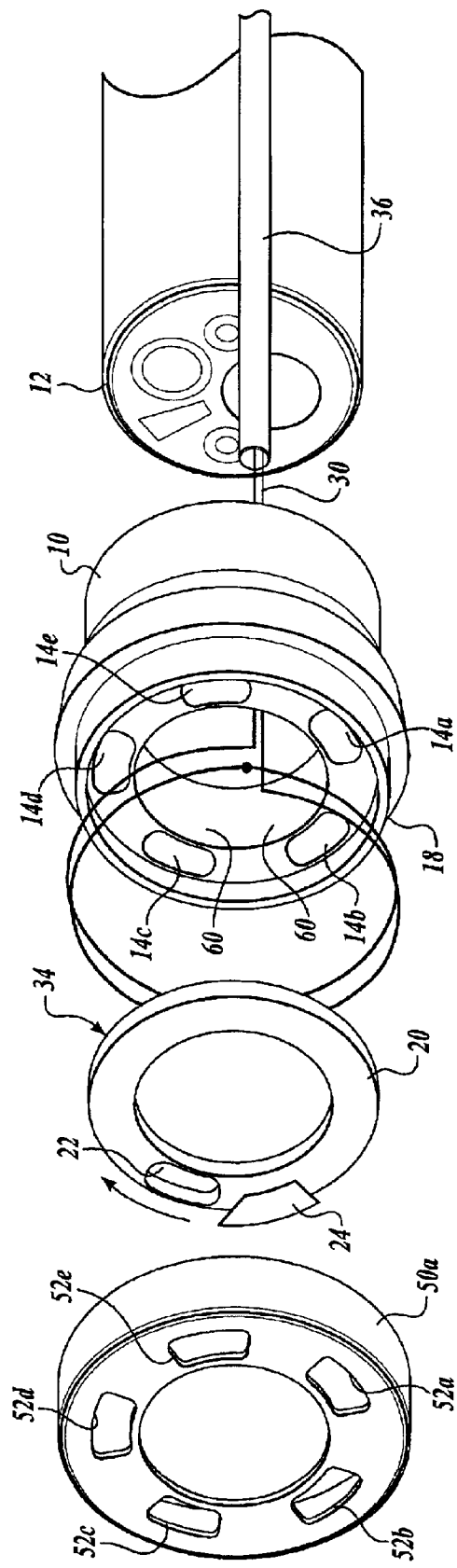
FIG. 1 is an exploded view of one embodiment of a multiple biopsy device according to the present invention.

In accordance with one embodiment of the present invention, a multiple biopsy device 10 comprises a cap that is fitted over the distal end of a conventional endoscope/bronchoscope 12 or other type of device that lets a physician visually examine internal body cavities. The biopsy device 10 has a lumen passing through the center with two different radiuses. At the proximal end, the lumen is sized such that it will snugly fit over the outer diameter of the endoscope. The lumen has a second, narrower, diameter toward the distal end that forms a step that engages the end of the endoscope such that the biopsy device cannot slide along the length of the endoscope. Preferably, the biopsy device 10 is made of a polymer or other biocompatible material and is secured to the distal end of the endoscope 12 with a friction fit.

The biopsy device 10 includes a number of chambers 14A, 14B, 14C . . . 14E disposed about its periphery. Each chamber has an opening that is oriented in the direction of the distal end of the endoscope for receiving tissue samples. Each of the chambers is isolated from the other chambers such that a tissue sample received in any single chamber does not commingle or interact with tissue samples received in any other chamber.

To obtain a tissue sample in the biopsy device, tissue is drawn into an individual chamber with a vacuum source or the like. A knife or cutter is passed over the opening of the chamber in order to cut the sample from a portion of the body and maintain it in place in the chamber.

In one embodiment of the invention, a rotating cap 20 moves a knife in front of each of the openings of the chambers to cut the tissue samples from the body. The cap 20 has an opening 22 that, when positioned in front of the a tissue chamber, allows tissue to enter the chamber. The biopsy device 10 has an annular ring 18 that surrounds the chambers 14A–14E and extends distally therefrom. The annular ring 18 forms a recess into which the rotating cap 20 is seated. Disposed across a portion of the opening 22 on the rotating cap 20 is a blade 24. When the cap 20 is rotated, tissue protruding through the opening 22 and into one of the biopsy chambers 14A–14E will be cut when the blade 24 is moved across the opening of the chamber.

In one embodiment of the invention, the cap 20 is rotated by an actuating thread 30 that winds around the perimeter of the cap in a groove or race 34 that is formed on the outer edge of the cap 20. In one embodiment of the invention, the actuating thread 30 forms a closed loop a portion of which extends to the proximal end of the endoscope 12. In one embodiment, the activating thread 30 extends through a catheter 36 that is positioned along the outside of the endoscope. Alternatively, the activating thread can be routed through an interior lumen of the endoscope 12. Under the control of a physician, the actuating thread is advanced such that the cap 20 is rotated within the area defined by the annular ring 18 and therefore around the openings of the biopsy chambers.

To maintain the rotating cap 20 in its seated position, a cover 50 having a number of openings 52A, 52B . . . 52E is placed over the rotating cap 20 and the annular ring 18. Each of the openings 52A–52E is aligned with the opening of a biopsy chamber 14A–14E.

Figure 2:
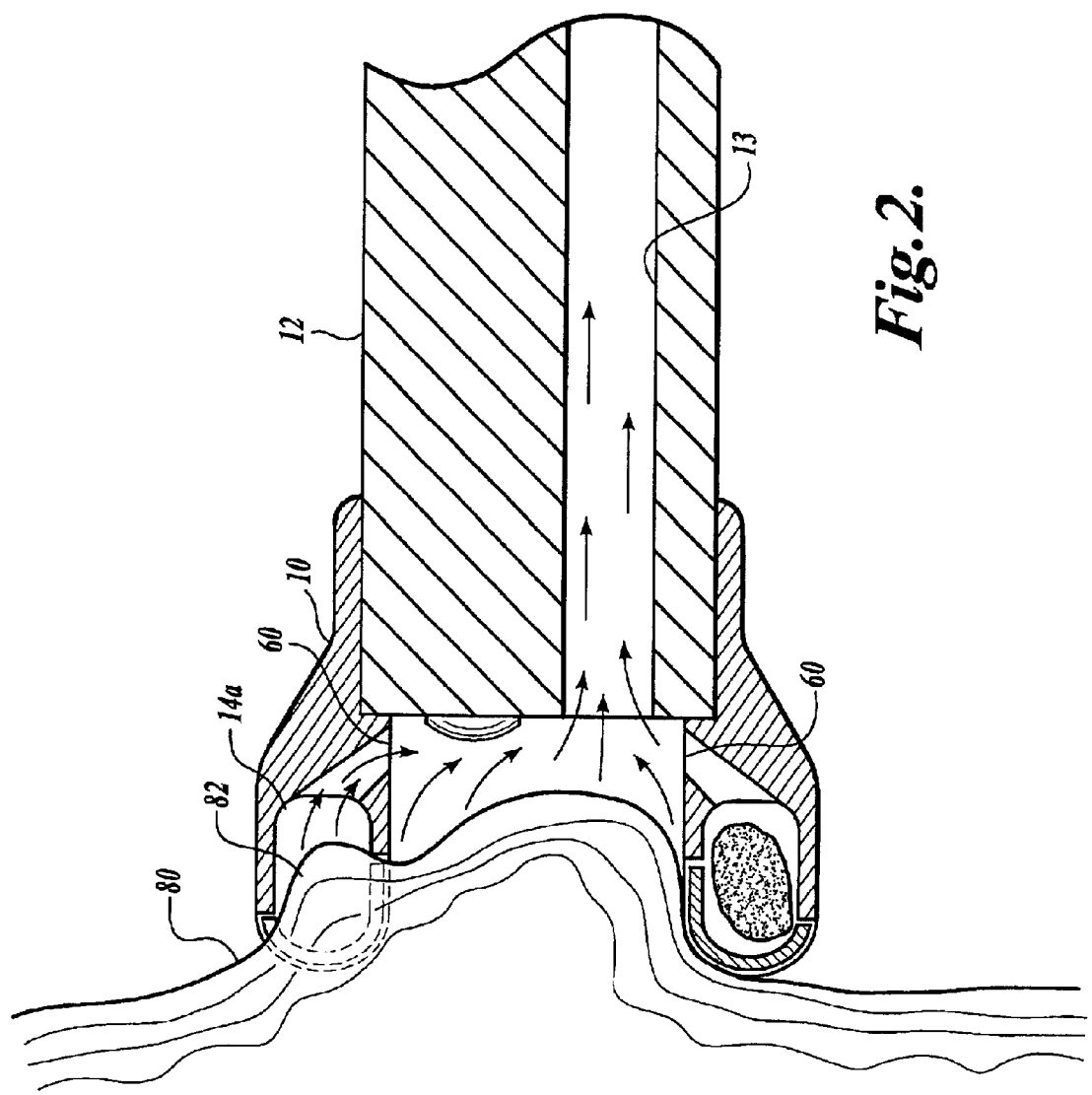
FIG. 2 illustrates how tissue is drawn into a biopsy chamber with a vacuum in accordance with one embodiment of the invention.

To draw tissue into the biopsy chambers, each chamber has one or more holes 60 that are in communication with a vacuum lumen 13 of the endoscope 12. As shown in FIG. 2, vacuum is applied from a location outside the body to the vacuum lumen 13 the endoscope 12. The vacuum pressure is conveyed to the biopsy chambers 14A–14D through the one or more holes 60.

In the currently preferred embodiment of the invention, all biopsy chambers are covered with the exception of the chamber that is aligned with the opening 22 in the rotating cap 20. Therefore, tissue 80 is drawn into the chamber that is aligned with the opening 22 in the rotating cap 20. The blade 24 is moved with respect to the biopsy chamber thereby cutting the tissue 82 suctioned into the chamber and sealing the chamber with the rear surface of the rotating cap as the opening 22 in the cap 20 is rotated past the chamber.

Once the tissue sample has been captured in the chamber, the hole 22 in the rotating cap 20 is advanced so that it aligns with the opening of another chamber in order to obtain another tissue sample.

Once the physician has obtained as many biopsy samples as desired, the endoscope can be withdrawn from the body and the biopsy device 10 removed from the distal end of the endoscope. Each of the biopsy chambers 14A–14E is preferably marked or coded so that the tissue samples can be traced to a particular location in a patient's body.

Although the presently preferred embodiment of the invention uses an actuating thread to rotate the cap 20 with respect to each individual biopsy chamber, it will be appreciated that other mechanisms such as a pneumatic or hydraulic actuator could be used to rotate the cap 20. Alternatively, the rotating cap 20 could be moved with piezoelectric or other type of motor or with ratcheting mechanisms. Alternatively, chambers could be made movable in the biopsy device such that the blade 24 remains stationary and the biopsy chambers moved underneath the blade in order to achieve the relative movement of the biopsy chambers against the blade in order to remove a tissue sample from the body.

While the preferred embodiment of the invention has been illustrated and described, it will be appreciated that various changes can be made therein without departing from the scope of the invention. For example, the blade 24 could be an electrosurgical device or laser. Similarly the biopsy device 10 may have more than one cutting device to remove more than one tissue sample at a time from a particular location the patient's body. It is therefore intended that the scope of the invention be determined from the following claims and equivalents thereto.

The embodiments of the invention in which an exclusive property or privilege is claimed are defined as follows:

1. A device for obtaining multiple biopsy samples from a patient, comprising:
    a cap that is secured to the distal end of an endoscope, the cap having a number of isolated biopsy chambers formed therein, each biopsy chamber having an opening through which tissue can enter the biopsy chamber;
    a cutter for cutting tissue that has entered the biopsy chamber;
    means for creating relative movement between the cutter and a single, isolated biopsy chamber of the number of biopsy chambers in order to cut tissue that has entered the single, isolated biopsy chamber.

2. The device of claim 1, wherein each biopsy chamber includes a port in fluid communication with a vacuum lumen of the endoscope such that when vacuum is applied to the vacuum lumen, tissue is drawn into one or more of the biopsy chambers.

3. The device of claim 1, wherein the means for creating relative movement between the cutter and the biopsy chamber comprises an actuating thread that moves the cutter relative to the openings of the biopsy chambers.

4. The device of claim 3, wherein the cutter is mounted on a rotating cap that is moved by the actuating thread over the openings of the biopsy chambers.

5. The device of claim 1, wherein each of the biopsy chambers is marked with a code or other identification.

6. The device of claim 1, wherein the means for creating relative movement between the cutter and the biopsy chambers moves the chambers with respect to the cutter.

7. A device for obtaining multiple biopsy samples from a patient, comprising:
    an endoscope having a proximal end and a distal end;
    a cap removably secured to the distal end of the endoscope, the cap having:
        a plurality of isolated biopsy chambers each of which has an opening in which a tissue sample can be received;
        a cutter for cutting tissue that enters an isolated biopsy chamber;
        a seal for closing a biopsy chamber once a tissue sample is cut and received in the isolated biopsy chamber; and
        an advancing mechanism for sequentially positioning the cutter over a single isolated biopsy chamber of the plurality of isolated biopsy chambers.

8. The device of claim 7, wherein
    the cutter is mounted on a ring that moves around the openings of the biopsy chambers.

9. The device of claim 8, wherein a surface of the ring forms a seal for at least some of the plurality of biopsy chambers.

10. A method of obtaining multiple biopsy samples from a patient, comprising:
    inserting an endoscope into a patient having a cap secured to the distal end of the endoscope, the cap including two or more isolated chambers;
    applying vacuum to a chamber to draw tissue into a single isolated chamber;
    moving the isolated chamber relative to a tissue cutter to cut tissue from the patient;
    sealing the isolated chamber before obtaining a tissue sample in another isolated chamber prior to removing the endoscope from the patient.

11. The method of claim 10, wherein the act of moving the chamber relative to a tissue cutter comprises:
    rotating the tissue cutter relative to the two or more chambers.

12. The method of claim 10, wherein the act of moving the chamber relative to the tissue cutter comprises:
    rotating the two or more chambers relative to the tissue cutter.

* * * * *

UNITED STATES PATENT AND TRADEMARK OFFICE
CERTIFICATE OF CORRECTION

PATENT NO. : 6,858,014 B2
DATED : February 22, 2005
INVENTOR(S) : J.J. Damarati

It is certified that error appears in the above-identified patent and that said Letters Patent is hereby corrected as shown below:

Title page,
Item [73], Assignee, "SciMed" should read -- SCIMED --

Signed and Sealed this

Nineteenth Day of July, 2005

JON W. DUDAS
*Director of the United States Patent and Trademark Office*